United States Patent
Ramesh et al.

(10) Patent No.: US 9,586,884 B2
(45) Date of Patent: Mar. 7, 2017

(54) METAL-DOPED HYDROXYAPATITE CATALYST

(71) Applicants: Agency for Science, Technology and Research, Singapore (SG); Nanyang Technological University, Singapore (SG)

(72) Inventors: Kanaparthi Ramesh, Jurong Island (SG); Armando Borgna, Jurong Island (SG); Yi Ling Eileen Goh, Singapore (SG); Timothy John White, Singapore (SG)

(73) Assignees: Agency for Science, Technology and Research, Singapore (SG); Nanyang Technological University, Singapore (SG)

( * ) Notice: Subject to any disclaimer, the term of this patent is extended or adjusted under 35 U.S.C. 154(b) by 0 days.

(21) Appl. No.: 14/780,678

(22) PCT Filed: Mar. 28, 2014

(86) PCT No.: PCT/SG2014/000145
§ 371 (c)(1),
(2) Date: Sep. 28, 2015

(87) PCT Pub. No.: WO2014/158096
PCT Pub. Date: Oct. 2, 2014

(65) Prior Publication Data
US 2016/0052851 A1     Feb. 25, 2016

(30) Foreign Application Priority Data
Mar. 28, 2013  (SG) .................. 201302352-8

(51) Int. Cl.
*C07C 45/38* (2006.01)
*B01J 27/00* (2006.01)
*B01J 27/198* (2006.01)
*B01J 23/50* (2006.01)
*B01J 27/18* (2006.01)
*B01J 27/188* (2006.01)
*B01J 35/10* (2006.01)

(52) U.S. Cl.
CPC .............. *C07C 45/38* (2013.01); *B01J 23/50* (2013.01); *B01J 27/1806* (2013.01); *B01J 27/188* (2013.01); *B01J 27/1817* (2013.01); *B01J 27/198* (2013.01); *B01J 35/1014* (2013.01)

(58) Field of Classification Search
CPC .............................. C07C 45/38; B01J 27/198
USPC .................................................. 568/471
See application file for complete search history.

(56) References Cited

U.S. PATENT DOCUMENTS

| | | |
|---|---|---|
| 6,323,383 B1 | 11/2001 | Tsuchida et al. |
| 2010/0275509 A1 | 11/2010 | Sakuma et al. |
| 2011/0190553 A1 | 8/2011 | Onda et al. |

FOREIGN PATENT DOCUMENTS

| | | |
|---|---|---|
| CN | 101906027 | 12/2010 |
| JP | 2002275116 | 9/2002 |
| WO | WO-2014/158096 | 10/2014 |

OTHER PUBLICATIONS

"International Application No. PCT/SG2014/000145, International Search Report and Written Opinion mailed May 21, 2014", (May 21, 2014), 9 pgs.

*Primary Examiner* — Sikarl Witherspoon
(74) *Attorney, Agent, or Firm* — Schwegman Lundberg & Woessner, P.A.

(57) ABSTRACT

The present invention provides the use of a metal-doped hydroxyapatite catalyst for highly selective conversion of an alcohol to an aldehyde at low temperatures. More specifically, the invention provides the use of a silver-doped hydroxyapatite catalyst for the highly selective oxidative dehydrogenation of ethanol to acetaldehyde. The present invention also provides the method for converting ethanol to acetaldehyde using a silver-doped hydroxyapatite catalyst.

18 Claims, 10 Drawing Sheets

METAL-DOPED HYDROXYAPATITE CATALYST

PRIORITY CLAIM TO RELATED APPLICATIONS

This application is a U.S. national stage application filed under 35 U.S.C. §371 from International Application Serial No. PCT/SG2014/000145, which was filed 28 Mar. 2014, and published as WO2014/158096 on 2 Oct. 2014, and which claims priority to Singapore Application No. 201302352-8, filed 28 Mar. 2013, which applications and publication are incorporated by reference as if reproduced herein and made a part hereof in their entirety, and the benefit of priority of each of which is claimed herein.

TECHNICAL FIELD

The present invention generally relates to the use of a metal-doped hydroxyapatite catalyst for the conversion of alcohol to aldehyde. The present invention also relates to a method of converting alcohols to aldehydes using such a metal-doped hydroxyapatite catalyst.

BACKGROUND

Acetaldehyde is an important precursor for the industrial production of high value chemicals such as pyridine derivatives, pentaerythritol, crotanaldehyde, acetic acid and vinyl acetate. Although acetaldehyde can be produced on an industrial scale from various routes such as oxidation of acetylene or ethylene via the Wacker process, hydration of acetylene, and vapour phase partial oxidation of butane, these processes all utilize an unstable or toxic starting material, often under high pressure, making them dangerous and costly for large-scale acetaldehyde production.

An alternative starting material for the production of acetaldehyde is ethanol. Ethanol is an attractive source for production of, high value chemicals because it can be produced economically and with low environmental impact via fermentation processes from renewable sources such as biomass feed stocks like corn, sugarcane and cellulose. In particular, second generation feed stocks such as lignocelluloses, wood chips, crop residues and tall grasses do not compete, with plant-based sources of food, making them cost-effective alternatives for renewable production of ethanol. Production of high value chemicals from ethanol is therefore currently attracting considerable interest because of the volatile prices of fossil fuel and concerns for the environment.

Reactions for converting ethanol to acetaldehyde include selective oxidation of ethanol (Eq.(1)) and oxidative dehydrogenation (Eq.(2)).

$$CH_3CH_2OH + \tfrac{1}{2}O_2 \rightarrow CH_3CHO + H_2O \quad \Delta H_{298} = 242 \text{ kJ/mol} \qquad \text{Eq.(1)}$$

$$2CH_3CH_2OH + \tfrac{1}{2}O_2 \rightarrow 2CH_3CHO + H_2O + H_2 \qquad \text{Eq.(2)}$$

However, the high temperature conditions required for the reactions described by Eq.(1) and Eq.(2) result in the production of significant amounts of carbon oxide by-products, described, for example, by Eq.(3), Eq.(4) and Eq.(5).

$$CH_3CH_2OH(g) + H_2O(g) \rightarrow 2CO(g) + 4H_2(g)$$
$$\Delta H_{298} = 256 \text{ kJ mol} \qquad \text{Eq.(3)}$$

$$CH_3CH_2OH(g) + \tfrac{1}{2}O_2 \rightarrow 2CO(g) + 2H_2(g) \quad \Delta H_{298} = 14 \text{ kJ/mol} \qquad \text{Eq.(4)}$$

$$CH_3CH_2OH(g) + \tfrac{1}{2}O_2(g) + 2H_2O(g) \rightarrow 2CO_2(g) + 5H_2(g)$$
$$\Delta H_{298} = 14 \text{ kJ/mol} \qquad \text{Eq.(5)}$$

The efficiency and selectivity of these reactions may be improved by the use of catalysts. However, catalysts for this reaction are known to be easily deactivated, require high reaction temperatures above 300° C. and have tendencies to produce various by-products which may decrease the yield and efficiency of the reaction. In general, even in the presence of catalysts, routes to convert ethanol to acetaldehyde are limited by selectivity, and conversion rates of greater than 80% are known to result in the formation, of mainly carbon oxide by-products. Above 0.200° C., the conversion selectivity to acetaldehyde decreases as the reaction temperature increases. These draw-backs make the conversion of ethanol to acetaldehyde on an industrial scale inefficient and costly.

Therefore, there is a need to provide an alternative catalyst to carry out the selective and efficient conversion of alcohols such as ethanol to aldehydes such as acetaldehyde. Further, there is a need for a method for selectively ad efficiently converting alcohols such as ethanol to aldehydes such as acetaldehyde.

SUMMARY

In a first aspect, there is provided a use of a metal-doped hydroxyapatite as a catalyst for converting an alcohol to an aldehyde. In an embodiment, the metal-doped hydroxyapatite may be silver-doped stoichiometric hydroxyapatite. In other embodiments, the alcohol may be ethanol and the aldehyde may be acetaldehyde.

Advantageously, the disclosed use of the metal-doped hydroxyapatite as a catalyst may facilitate the efficient, conversion of an alcohol such as ethanol to an aldehyde such as acetaldehyde. This may provide an alternate route for producing acetaldehyde, which is a precursor for high-value chemicals such as pyridine derivatives, pentaerythritol, crotanaldehyde, acetic acid and vinyl acetate, from ethanol. Further advantageously, the use of a metal-doped hydroxyapatite as a catalyst to convert ethanol to acetaldehyde may circumvent the use of costly and dangerous conventional methods for producing acetaldehyde, which may require the use of unstable or toxic starting materials.

Further advantageously, the disclosed use of a metal-doped hydroxyapatite as a catalyst may increase the conversion, yield and selectivity of the conversion of ethanol to acetaldehyde. The catalyst may facilitate a higher conversion rate from ethanol to acetaldehyde, which may result in an increased amount of ethanol being converted to acetaldehyde. More advantageously, increasing the selectivity of the reaction may result in higher acetaldehyde yield due to less by-products being formed.

In an embodiment, the alcohol may be oxidised to the aldehyde. Advantageously, the oxidation may be an oxidative dehydrogenation reaction. Advantageously, the oxidative dehydrogenation reaction of ethanol to acetaldehyde may result in decreased formation of by-products, as compared to selective oxidation of ethanol, increasing the yield and efficiency of the reaction.

Even further advantageously, the disclosed use of a metal doped hydroxyapatite may have improved stability as a catalyst. That is, the catalyst may remain active without becoming deactivated over a longer period of time, compared to conventional catalysts for the same reaction.

Further advantageously, the disclosed use of a metal-doped hydroxyapatite as a catalyst for converting ethanol to acetaldehyde may depend on the nature of the active phase and the properties of the support material of the catalyst. The interplay of properties between the active phase such as silver and the support material such as HAP may be crucial for the efficacy and stability of, the catalyst in converting ethanol to acetaldehyde. The selectivity of the conversion reaction may be improved by isolation of the active site or the reaction site of the catalyst by dispersing it on a support such as HAP. In a second aspect, there is provided a method for converting an alcohol to an aldehyde, comprising the step of contacting the alcohol with a metal-doped hydroxyapatite catalyst as mentioned above. In other embodiments, the alcohol may be ethanol and the aldehyde may be acetaldehyde.

Advantageously, the disclosed method for converting an alcohol such as ethanol to an aldehyde such as acetaldehyde may allow the conversion to be performed at low temperatures below 300° C. This may circumvent the problem faced by conventional methods of converting ethanol to acetaldehyde, where high reaction temperatures are required, consequently resulting in the increased production of by-products and a decrease in reaction yield and efficiency.

Further advantageously, the disclosed method for converting ethanol to acetaldehyde may allow the conversion to be performed at atmospheric pressure. This may circumvent the problem of conventional methods where the reaction must be performed under high pressures.

DEFINITIONS

The following words and terms used herein shall have the meaning indicated:

The term "conversion" refers to a chemical reaction process in which chemical transformation takes place, that is, the product differs chemically from the starting materials.

The term "conversion" also refers to the percentage of reactants converted to products inside a chemical reactor. It describes, as ratios, how much of a reactant has reacted (X conversion, normally between zero and one), how much of a desired product was formed (Y—yield, normally also between zero and one) and how much desired product was formed in ratio to the undesired product(s) (S—selectivity). The terms "convert" and "converting" should be construed accordingly.

The term "active phase" refers to a catalytically active component, being a part of a catalyst along with the other major components such as a support or carrier.

The terms "support" and "carrier" for the purposes of this disclosure, may be used interchangeably to refer to a material, usually a solid with a high surface area, to which a catalyst is affixed onto or embedded within. The support may be inert or participate in the catalytic reactions.

The term "high temperature" for the purposes of this disclosure, refers to reaction temperatures above 300° C.

The term "low temperature" for the purposes of this disclosure, refers to reaction temperatures below 300° C.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inClusion of additional, unrecited elements.

As used herein, the terms "about" and "approximately", in the context of concentrations of components of the formulations, or where applicable, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure of Optional Embodiments

Illustrative, non-limiting embodiments of a use of a metal-doped hydroxyapatite in accordance with the first aspect will now be disclosed.

The metal-doped hydroxyapatite may be used as a catalyst for converting an alcohol to an aldehyde.

The dopant of the metal-doped hydroxyapatite may be selected from the group consisting of a metal, a metal oxide and mixtures thereof. The metal, metal oxide and mixtures thereof may be referred to as the active phase. The particle size of the active catalytic phase may be in the nanoscale. The active catalytic phase may comprise less than 15% of the total weight of the catalyst. A catalyst may lose its activity and/or selectivity if the active phase is subjected to any structural or compositional changes, or is blocked by reaction products, or if the active surface area is reduced as a result of sintering or migration of the active phase particles.

The metal may be a transition metal. The transition metal may be a group 3, group 4, group 5, group 6, group 10, group 11 or group 12 transition metal. The transition metal may be scandium (Sc), yttrium (Y), lutetium (Lu), lawrencium (Lr), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), nickel (Ni), palladium (Pd), platinum (Pt), copper (Cu), silver (Ag), gold (Au), zinc (Zn), cadmium (Cd) or mercury (Hg). The transition metal may be silver, gold, vanadium or chromium. The transition metal may be silver. The silver may have an oxidation state of +1, +2, +3 or +4. The gold may have an oxidation state of +1, +2, +3 or +5. The vanadium may have an oxidation state of +1, +2, +3, +4 or +5. Chromium may have an oxidation state of +1, +2, +3, +4, +5 or +6.

The metal oxide may be an oxide of a transition metal. The oxide of a transition metal may be an oxide of a group 3, group 4, group 5, group 6, group 10, group 11 or group 12 transition metal. The oxide of a transition metal may be an oxide of scandium (Sc), yttrium (Y), lutetium (Lu), lawrencium (Lr), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), nickel (Ni), palladium (Pd), platinum (Pt), copper (Cu), silver (Ag), gold (Au), zinc (Zn), cadmium (Cd) or mercury (Hg). The oxide of a transition metal may be an oxide of silver, gold, vanadium or chromium. The oxide of a transition metal may be an oxide of silver. The oxide of silver may be silver(I) oxide ($Ag_2O$), silver(II) oxide (AgO) or silver(I,III) oxide ($Ag_4O_4$). The oxide of gold may be gold(I) oxide ($Au_2O$), gold(II) oxide (AuO) or gold(III) oxide ($Au_2O_3$). The oxide of vanadium may be vanadium(II) oxide (VO), vanadium (III) oxide ($V_2O_3$), vanadium(IV) oxide ($VO_2$) or vanadium (V) oxide ($V_2O_5$). The oxide of chromium may be chromium(II) oxide (CrO), chromium(III) oxide ($Cr_2O_3$) chromium (IV) oxide ($CrO_2$), chromium (VI) oxide ($CrO_3$), chromium (VI) oxide peroxide ($CrO_5$) or mixed valence species of chromium oxides such as $Cr_3O_{21}$.

Calcium hydroxyapatite (HAP; $Ca_{10}(PO_4)_6(OH)_2$) is currently attracting considerable interest for applications in chromatography, bioengineering and catalysis. The utility of the material may be broadened by partial replacement of $Ca^{2+}$ ions with transvalent metals. Consequently, HAP may be tailored as an active solid catalyst or as a support or carrier with readily tuneable surface properties. HAP may crystallize with hexagonal $P6_3/m$ symmetry with $Ca^{2+}$ arranged in two non-equivalent sites, I and II, with the Ca(I) ions aligned in columns while the Ca(II) ions may be in equilateral triangles centred on a screw axis surrounded with the $PO_4^{3-}$ tetrahedra. HAP may exhibit both acidic and basic properties in its crystal lattice form, together with important properties such as high adsorption capacity and ion-exchange capabilities.

The hydroxyapatite may be a stoichiometric hydroxyapatite or a non-stoichiometric hydroxyapatite. The stoichiometric HAP may have a Ca/P molar ratio of 1.67. The non-stoichiometric HAP may have a Ca/P molar ratio in the range of about 1.45 to about 1.70, about 1.45 to about 1.50, about 1.45 to about 1.55, about 1.45 to about 1.65, about 1.50 to about 1.55, about 1.50 to about 1.60, about 1.50 to about 1.65, about 1.50 to about 1.70, about 1.55 to about 1.60, about 1.55 to about 1.65, about 1.55 to about 1.70, about 1.60 to about 1.65, about 1.60 to about 1.70 or about 1.65 to about 1.70. The non-stoichiometric HAP may have a Ca/P molar ratio in the range of about 1.50 to about 1.65.

The stoichiometric HAP may possess mainly basic sites, while the non-stoichiometric HAP may exhibit predominantly acidic properties. Thus, non-stoichiometric HAP may act as an acidic catalyst suitable for ethanol dehydration yielding products such as ethylene, while stoichiometric HAP may be suitable for catalysing reactions such as oxidative dehydrogenation of ethanol to produce acetaldehyde. Surface P—OH groups may play an important role in tuning properties such as dispersion of nanoparticles on the HAP.

Support materials such as HAP provide a carrier for the active metal or metal oxide phases such as silver or oxides of silver. The reactivity of heterogeneous catalysts and nanomaterial-based catalysts may occur at the surface atoms. Consequently, it may be advantageous to maximize the surface area of a catalyst by distributing it over the support. The support may be inert or may participate in the catalytic reactions.

The physical and chemical properties of the support material along with the interaction between the metal and the support material may play a crucial role in the development of active oxidation catalysts. For example, selectivity of the conversion reaction may be improved by isolation of the active site or the reaction site of the catalyst. This may be done by using a support such as HAP to disperse and isolate the active site of the catalyst. Further, less catalyst is required to catalyse the reaction when it is dispersed on a support such as HAP. This may lead to reduced costs for preparing the catalyst.

The hydroxyapatite may be, doped with the metal, metal oxide or mixtures thereof, at an atomic percentage of up to 10 at %. The hydroxyapatite may be doped with the metal, metal oxide or mixtures thereof, at an atomic percentage of up to 6 at %. The hydroxyapatite may be doped with the metal, metal oxide or mixtures thereof, at an atomic percentage in the range of about 0.01% to about 10%, about 0.01% to about 0.1%, about 0.01% to about 1%, about 0.01% to about 2%, about 0.01% to about 4%, about 0.01% to about 6%, about 0.01% to about 8%, about 0.1% to about 1%, about 0.1% to about 2%, about 0.1% to about 4%, about 0.1% to about 6%, about 0.1% to about 8%, about 0.1% to about 10%, about 1% to about 2%, about 1% to about 4%, about 1% to about 6%, about 1% to about 8%, about 1% to about 10%, about 2% to about 4%, about 2% to about 6%, about 2% to about 8%, about 2% to about 10%, about 4% to about 6%, about 4% to about 8%, about 4% to about 10%, about 6% to about 8%, about 6% to about 10% or about 8% to about 10%.

The conversion of alcohol to acetaldehyde may comprise oxidation of the alcohol to aldehyde. The oxidation may be an oxidative dehydrogenation. During the oxidative dehydrogenation, hydrogen may be removed from the alcohol to yield the aldehyde. The general oxidative dehydrogenation of an alcohol to aldehyde may be represented by the following formula:

$$2R\text{—}CH_2OH + \tfrac{1}{2}O_2 \rightarrow 2R\text{—}CHO + H_2O + H_2$$

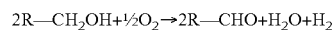

where R is any group in which a carbon or a hydrogen atom is attached to the rest of the molecule.

The alcohol may be a lower alcohol of 1 to 6 carbon atoms. The alcohol may be a lower alcohol of 1, 2, 3, 4, 5 or 6 carbon atoms. The alcohol may be methanol, ethanol, propanol, butanol, pentanol or hexanol as well as isomers thereof. The propanol may be propan-1-ol. The butanol may be butan-1-ol. The pentanol may be pentan-1-ol, 3-methylbutan-1-ol, 2-methylbutan-1-ol or 2,2-dimethylpropan-1-ol. The hexanol may be hexan-1-ol, 2-methylpentan-1-ol, 3-methylpentan-1-ol, 4-methylpentan-1-ol, 2,2-dimethylbutan-1-ol, 2,3-dimethylbutan-1-ol, 3,3-dimethylbutan-1-ol or 2-ethylbutan-1-ol. The alcohol may be ethanol.

The aldehyde may be a lower aldehyde of 1 to 6 carbon atoms. The aldehyde may be a lower aldehyde of 1, 2, 3, 4, 5 or 6 carbon atoms. The aldehyde may be formaldehyde, acetaldehyde, propionaldehyde, butyraldehyde, pentanaldehyde or hexanaldehyde as well as is isomers thereof. The propionaldehyde may be propan-1-al. The butyraldehyde may be butan-1-al. The pentanaldehyde may be pentan-1-al, 3-methylbutan-1-al, 2-methylbutan-1-al or 2,2-dimethylpropan-1-al. The hexanaldehyde may be hexan-1-al, 2-methylpentan-1-al, 3-methylpentan-1-al, 4-methylpentan-1-al, 2,2-dimethylbutan-1-al, 2,3-dimethylbutan-$1_7$ al, 3,3-dimethylbutan-1-al or 2-ethylbutan-1-al. The aldehyde may be acetaldehyde.

The oxidative dehydrogenation of ethanol to acetaldehyde may be represented by the following formula:

$$2CH_3CH_2OH + \tfrac{1}{2}O_2 \rightarrow 2CH_3CHO + H_2O + H_2.$$

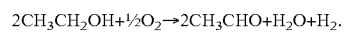

Oxidative dehydrogenation of ethanol may result in improved selectivity for acetaldehyde over carbon oxide by-products.

Illustrative, non-limiting embodiments of a method for converting an alcohol to an aldehyde in accordance with the second aspect will now be disclosed.

A method for converting an alcohol to an aldehyde may comprise the step of contacting the alcohol with a metal-doped hydroxyapatite catalyst disclosed above, to form the aldehyde.

The contacting step may be performed at a temperature in the range of about 150° C. to about 350° C., about 150° C. to about 175° C., about 150° C. to about 200° C., about 150° C. to about 225° C., about 150° C. to about 250° C., about 150° C. to about 275° C., about 150° C. to about 300° C., about 150° C. to about 325° C., about 175° C. to about 200° C., about 175° C. to about 225° C., about 175° C. to about 250° C., about 175° C. to about 275° C., about 175° C. to about 300° C., about 175° C. to about 325° C., about 175° C. to about 350° C., about 200° C. to about 225° C., about 200° C. to about 250° C., about 200° C. to about 275° C., about 200° C. to about 300° C., about 200° C. to about 325° C., about 200° C. to about 350° C., about 225° C. to about 250° C., about 225° C. to about 275° C., about 225° C. to about 300° C., about 225° C. to about 325° C., about 225° C. to about 350° C., about 250° C. to about 275° C., about 250° C. to about 300° C., about 250° C. to about 325° C., about 250° C. to about 350° C., about 275° C. to about 300° C., about 275° C. to about 325° C., about 275° C. to about 350° C., about 300° C. to about 325° C., about 300° C. to about 350° C. or 325° C. to about 350° C. The contacting step may be performed at a temperature in the range of about 200° C. to about 275° C.

The contacting step may be performed at atmospheric pressure or higher. The contacting step may be performed at a pressure in the range of about 1 atm to about 20 atm, about 1 atm to about 2 atm, about 1 atm to about 5 atm, about 1 atm to about 10 atm, about 2 atm to about 5 atm, about 2 atm to about 10 atm, about 2 atm to about 20 atm, about 5 atm to about 10 atm, about 5 atm to about 20 atm or about 10 atm to about 20 atm. The contacting step may be performed at 1-atm. The contacting step may be performed at pressures higher than 1 atm, but pressures at or about 1 atm may be preferred due to thermodynamic considerations.

The contacting step may be performed at a liquid hourly space velocity (LHSV) in the range of about 0.5 $h^{-1}$ to about 15 $h^{-1}$, about 0.5 $h^{-1}$ to about 1 $h^{-1}$, about 0.5 $h^{-1}$ to about 2 $h^{-1}$, about 0.5 $h^{-1}$ to about 4 $h^{-1}$, about 0.5 $h^{-1}$ to about 6 $h^{-1}$, about 0.5 $h^{-1}$ to about 8 $h^{-1}$, about 0.5 $h^{-1}$ to about 10 $h^{-1}$, about 0.5 $h^{-1}$ to about 12 $h^{-1}$, about 0.5 $h^{-1}$ to about 14 $h^{-1}$, about 1 $h^{-1}$ to about 2 $h^{-1}$, about 1 $h^{-1}$ to about 4 $h^{-1}$, about 1 $h^{-1}$ to about 6 $h^{-1}$, about 1 $h^{-1}$ to about 8 $h^{-1}$, about 1 $h^{-1}$ to about 10 $h^{-1}$, about 1 $h^{-1}$ to about 12 $h^{-1}$, about 1 $h^{-1}$ to about 14 $h^{-1}$, about 1 $h^{-1}$ to about 15 $h^{-1}$, 2 $h^{-1}$ to about 4 $h^{-1}$, about 2 $h^{-1}$ to about 6 $h^{-1}$, about 2 $h^{-1}$ to about 8 $h^{-1}$, about 2 $h^{-1}$ to about 10 $h^{-1}$, about 2 $h^{-1}$ to about 12 $h^{-1}$, about 2 $h^{-1}$ to about 14 $h^{-1}$, about 2 $h^{-1}$ to about 15 $h^{-1}$, about 4 $h^{-1}$ to about 6 $h^{-1}$, about 4 $h^{-1}$ to about 8 $h^{-1}$, about 4 $h^{-1}$ to about 10 $h^{-1}$, about 4 $h^{-1}$ to about 12 $h^{-1}$, about 4 $h^{-1}$ to about 14 $h^{-1}$, about 4 $h^{-1}$ to about 15 $h^{-1}$, about 6 $h^{-1}$ to about 8 $h^{-1}$, about 6 $h^{-1}$ to about 10 $h^{-1}$, about 6 $h^{-1}$ to about 12 $h^{-1}$, about 6 $h^{-1}$ to about 14 $h^{-1}$, about 6 $h^{-1}$ to about 15 $h^{-1}$, about 8 $h^{-1}$ to about 10 $h^{-1}$, about 8 $h^{-1}$ to about 12 $h^{-1}$, about 8 $h^{-1}$ to about 14 $h^{-1}$, about 8 $h^{-1}$ to about 15 $h^{-1}$, about 10 $h^{-1}$ to about 12 $h^{-1}$, about 10 $h^{-1}$ to about 14 $h^{-1}$, about 10 $h^{-1}$ to about 15 $h^{-1}$, about 12 $h^{-1}$ to about 14 $h^{-1}$, about 12 $h^{-1}$ to about 15 $h^{-1}$ or about 14 $h^{-1}$ to about 15 $h^{-1}$. The contacting step may be performed at a liquid hourly space velocity (LHSV) in the range of about 1.5 $h^{-1}$ to about 9 $h^{-1}$.

The contacting step may be performed at a weight hourly space velocity (WHSV) in the range of about 1 $h^{-1}$ to about 10 $h^{-1}$, 1 $h^{-1}$ to about 2 $h^{-1}$, 1 $h^{-1}$ to about 3 $h^{-1}$, 1 $h^{-1}$ to about 4 $h^{-1}$, 1 $h^{-1}$ to about 5 $h^{-1}$, 1 $h^{-1}$ to about 6 $h^{-1}$, 1 $h^{-1}$ to about 7 $h^{-1}$, 1 $h^{-1}$ to about 8 $h^{-1}$, 1 $h^{-1}$ to about 9 $h^{-1}$, 2 $h^{-1}$ to about 3 $h^{-1}$, 2 $h^{-1}$ to about 4 $h^{-1}$, 2 $h^{-1}$ to about 5 $h^{-1}$, 0.2 $h^{-1}$ to about 6 $h^{-1}$, 2 $h^{-1}$ to about 7 $h^{-1}$, 2 $h^{-1}$ to about 8 $h^{-1}$, 2 $h^{-1}$ to about 9 $h^{-1}$, 2 $h^{-1}$ to about 10 $h^{-1}$, 3 $h^{-1}$ to about 4 $h^{-1}$, 3 $h^{-1}$ to about 5 $h^{-1}$, 3 $h^{-1}$ to about 6 $h^{-1}$, 3 $h^{-3}$ to about 7 $h^{-1}$, 3 $h^{-1}$ to about 8 $h^{-1}$, 3 $h^{-1}$ to about 9 $h^{-1}$, 3 $h^{-1}$ to about 10 $h^{-1}$, 4 $h^{-1}$ to about 5 $h^{-1}$, 4 $h^{-1}$ to about 6 $h^{-1}$, 4 $h^{-1}$ to about 7 $h^{-1}$, 4 $h^{-1}$ to about 8 $h^{-1}$, 4 $h^{-1}$ to about 9 $h^{-1}$, 4 $h^{-1}$ to about 10 $h^{-1}$, 5 $h^{-1}$ to about 6 $h^{-1}$, 5 $h^{-1}$ to about 7 $h^{-1}$, 5 $h^{-1}$ to about 8 $h^{-1}$, 5 $h^{-1}$ to about 9 $h^{-1}$, 5 $h^{-1}$ to about 10 $h^{-1}$, 6 $h^{-1}$ to about 7 $h^{-1}$, 6 $h^{-1}$ to about 8 $h^{-1}$, 6 $h^{-1}$ to about 9 $h^{-1}$, 6 $h^{-1}$ to about 10 $h^{-1}$, 7 $h^{-1}$ to about 8 $h^{-1}$, 7 $h^{-1}$ to about 9 $h^{-1}$, 7 $h^{-1}$ to about 10 $h^{-1}$, 8 $h^{-1}$ to about 9 $h^{-1}$, 8 $h^{-1}$ to about 10 $h^{-1}$ or 9 $h^{-1}$ to about 10 $h^{-1}$. The contacting step may be performed at a weight hourly space velocity (WHSV) in the range of about 4 $h^{-1}$ to about 7 $h^{-1}$.

The contacting step may performed at an ethanol flow rate in the range of about 0.005 mL/min to about 0.055 mL/min, about 0.005 mL/min to about 0.015 mL/min, about 0.005 mL/min to about 0.025 mL/min, about 0.005 mL/min to about 0.035 mL/min, about 0.005 mL/min to about 0.045 mL/min, about 0.015 mL/min to about 0.025 mL/min, about 0.015 mL/min to about 0.035 mL/min, about 0.015 mL/min to about 0.045 mL/min, about 0.015 mL/min to about 0.055 mL/min, about 0.025 mL/min to about 0.035 mL/min, about 0.025 mL/min to about 0.045 mL/min, about 0.025 mL/min to about 0.055 mL/min, about 0.035 mL/min to about 0.045 mL/min, about 0.035 mL/min to about 0.055 mL/min or about 0.045 mL/min to about 0.055 mL/min. The contacting step may be performed at an ethanol flow rate of about 0.025 mL/min.

The contacting step may be performed at a synthetic air flow rate in the range of about 30.0 mL/min to about 90.0 mL/min, about 30.0 mL/min to about 40.0 mL/min, about 30.0 mL/min to about 50.0 mL/min, about 30.0 mL/min to about 60.0 mL/min, about 30.0 mL/min to about 70.0 mL/min, about 30.0 mL/min to about 80.0 mL/min, about 40.0 mL/min to about 50.0 mL/min, about 40.0 mL/min to about 60.0 mL/min, about 40.0 mL/min to about 70.0 mL/min, about 40.0 mL/min to about 80.0 mL/min, about 40.0 mL/min to about 90.0 mL/min, about 50.0 mL/min to about 60.0 mL/min, about 50.0 mL/min to about 70.0 mL/min, about 50.0 mL/min to about 80.0 mL/min, about 50.0 mL/min to about 90.0 mL/min, about 60.0 mL/min to about 70.0 mL/min, about 60.0 mL/min to about 80.0 mL/min, about 60.0 mL/min to about 90.0 mL/min, about 70.0 mL/min to about 80.0 mL/min, about 70.0 mL/min to about 90.0 mL/min or about 80.0 mL/min to about 90.0 mL/min. The contacting step may be performed at a synthetic air flow rate of about 60.0 mL/min.

The contacting step may be performed at a purified air flow rate in the range of about 20.0 mL/min to about 60.0 mL/min, about 20.0 mL/min to about 30.0 mL/min, about 20.0 mL/min to about 40.0 mL/min, about 20.0 mL/min to about 50.0 mL/min, about 30.0 mL/min to about 40.0 mL/min, about 30.0 mL/min to about 50.0 mL/min, about 30.0 mL/min to about 60.0 mL/min, about 40.0 mL/min to about 50.0 mL/min, about 40.0 mL/min to about 60.0 mL/min or about 50.0 mL/min to about 60.0 mL/min. The contacting step may be performed at a purified air flow rate of about 40.0 mL/min.

The contacting step may be performed at an oxygen flow rate in the range of about 6.0 mL/min to about 18.0 mL/min, about 6.0 mL/min to about 8.0 mL/min, about 6.0 mL/min to about 10.0 mL/min, about 6.0 mL/min to about 12.0 mL/min, about 6.0 mL/min to about 14.0 mL/min, about 6.0 mL/min to about 16.0 mL/min, about 8.0 mL/min to about 10.0 mL/min, about 8.0 mL/min to about 12.0 mL/min, about 8.0 mL/min to about 14.0 mL/min, about 8.0 mL/min to about 16.0 mL/min, about 8.0 mL/min to about 18.0 mL/min, about 10.0 mL/min to about 12.0 mL/min, about 10.0 mL/min to about 14.0 mL/min, about 10.0 mL/min to about 16.0 mL/min, about 10.0 mL/min to about 18.0 mL/min, about 12.0 mL/min to about 14.0 mL/min, about 12.0 mL/min to about 16.0 mL/min, about 12.0 mL/min to about 18.0 mL/min, about 14.0 mL/min to about 16.0 mL/min, about 14.0 mL/min to about 18.0 mL/min or about 16.0 mL/min to about 18.0 mL/min. The contacting step may be performed at an oxygen flow rate of about 12.0 mL/min.

The contacting step may comprise oxidation of the alcohol to aldehyde. The oxidation may be an oxidative dehydrogenation. During the oxidative dehydrogenation, hydrogen may be removed from the alcohol to yield the aldehyde. The general oxidative dehydrogenation of an alcohol to aldehyde may be represented by the following formula:

$$2R\text{---}CH_2OH + \tfrac{1}{2}O_2 \rightarrow 2R\text{---}CHO + H_2O + H_2$$

where R is any group in which a carbon or a hydrogen atom is attached to the rest of the molecule.

The alcohol may be a lower alcohol of 1 to 6 carbon atoms. The alcohol may be a lower alcohol of 1, 2, 3, 4, 5 or 6 carbon atoms. The alcohol may be methanol, ethanol, propanol, butanol, pentanol or hexanol as well as isomers thereof. The propanol may be propan-1-ol. The butanol may be butan-1-ol. The pentanol may be pentan-1-ol, 3-methylbutan-1-ol, 2-methylbutan-1-ol or 2,2-dimethylpropan-1-ol. The hexanol may be hexan-1-ol, 2-methylpentan-1-ol, 3-methylpentan-1-ol, 4-methylpentan-1-ol, 2,2-dimethylbutan-1-ol, 2,3-dimethylbutan-1-ol, 3,3-dimethylbutan-1-ol or 2-ethylbutan-1-ol. The alcohol may be ethanol.

The aldehyde may be a lower aldehyde of 1 to 6 carbon atoms. The aldehyde may be a lower aldehyde of 1, 2, 3, 4, 5 or 6 carbon atoms. The aldehyde may be formaldehyde, acetaldehyde, propionaldehyde, butyraldehyde, pentanaldehyde or hexanaldehyde as well as isomers thereof. The propionaldehyde may be propan-1-al. The butyraldehyde may be butan-1-al. The pentanaldehyde may be pentan-1-al, 3-methylbutan-1-al, 2-methylbutan-1-al or 2,2-dimethylpropan-1-al. The hexanaldehyde may be hexan-1-al, 2-methylpentan-1-al, 3-methylpentan-1-al, 4-methylpentan-1-al, 2,2-dimethylbutan-1-al, 2,3-dimethylbutan-1-al, 3,3-dimethylbutan-1-al or 2-ethylbutan-1-al. The aldehyde may be acetaldehyde.

The oxidative dehydrogenation of ethanol to acetaldehyde may be represented by the following formula:

$$2CH_3CH_2OH + \tfrac{1}{2}O_2 \rightarrow 2CH_3CHO + H_2O + H_2.$$

Oxidative dehydrogenation of ethanol may result in improved selectivity for acetaldehyde over carbon oxide by-products.

BRIEF DESCRIPTION OF DRAWINGS

The accompanying drawings illustrate disclosed embodiments and serve to explain the principles of the disclosed embodiments. It is to be understood, however, that the drawings are designed for purposes of illustration only, and not as a definition of the limits of the invention.

EXAMPLES

Figure 1:
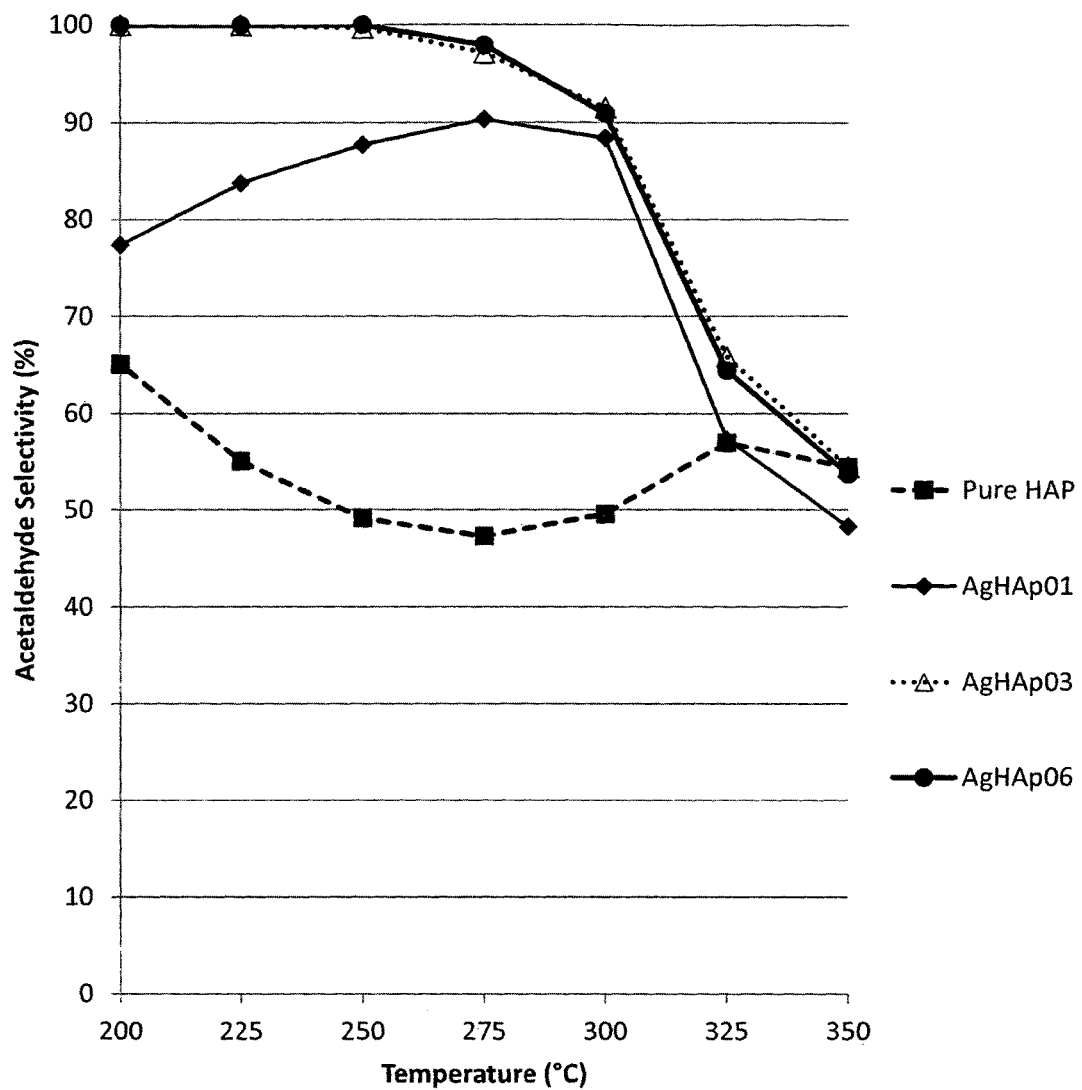
FIG. 1 is a graph showing the acetaldehyde selectivity of the ethanol conversion over various HAP catalysts with different Ag content (0, 1, 3 and 6 at %) at reaction temperatures between 200° C. and 350° C.

Non-limiting examples of the invention will be further described in greater detail by reference to specific Examples, which should not be construed as in any way limiting the scope of the invention. Based on the foregoing disclosure, it should be clear that by the method, the objectives set forth herein can be fulfilled. It is, therefore, to be understood that any variations evidently falling within the scope of the claimed invention and thus, the selection of specific device or apparatus, and specific metals modified on the HAP support can be determined without departing from the scope of the disclosure. Thus, the scope of the disclosure should include all modification and variation that may fall within the scope of the claims.

Example 1

Preparation of the Ag-Doped HAP

Materials:

Analytical grade calcium hydroxide ($Ca(OH)_2$), analytical grade silver nitrate ($AgNO_3$) and analytical grade phosphoric acid ($H_3PO_4$ (85 wt %)) were obtained from commercial sources and used without further purification.

Preparation Procedure:

Samples of pure HAP and Ag-doped HAP were prepared by a co-precipitation route. The general formula of calcium hydroxyapatite can be expressed as:

$$Ca_{10-x}Ag_x(PO_4)_6(OH)_2, \text{ where } 0 \leq x \leq 0.6.$$

In a typical preparation method for pure HAP, $Ca(OH)_2$ powder was suspended in deionised water followed by addition of $AgNO_3$ into the suspension in stoichiometric amount. In a typical preparation method for Ag-doped HAP, $Ca(OH)_2$ powder was suspended in deionised water followed by addition of $AgNO_3$ into the suspension in stoichiometric amount. For both pure and Ag-doped HAP, 0.1 M $H_3PO_4$ was dispensed from a burette into the suspension containing the metal ions at room temperature with constant magnetic stirring. After all the $H_3PO_4$ was added, the mixture (precursor solution) was warmed and maintained at 70° C. for 90 minutes. The mixture was subsequently transferred to an oven at 100° C. for 2 hours. The mixture was then removed from the oven and aged overnight at room temperature. The precipitate from this mixture was washed repeatedly with deionized water and filtered under vacuum. The final precipitate was obtained after drying the wet precipitate in an oven at 100° C. overnight and grinding with an agate mortar and pestle to obtain a fine homogeneous pure or Ag-doped HAP powder. The resultant pre or Ag-doped HAP powder was loaded in an alumina crucible and calcined in a gas tube furnace under flowing oxygen at 600° C. for 1 hour.

TABLE 1

The physical characterisation of pure HAP and Ag-doped HAP.

| Catalyst | Ag content (at %) | BET specific surface area (m²/g) |
|---|---|---|
| Pure HAP | 0 | 75 |
| 1 at % Ag-HAP | 1 | 65 |
| 3 at % Ag-HAP | 3 | 70 |
| 6 at % Ag-HAP | 6 | 41 |

Table 1 shows some of the physical characteristics of the prepared pure and Ag-doped HAP. The Brunauer-Emmett-Teller (BET) surface areas were measured using the $N_2$ physisorption method, and shows that the pure HAP has a BET surface area of 75 m²/g which decreases with increasing Ag-content. The HAP sample with 6 at % Ag showed a BET surface area of only 41 m²/g. The decrease in surface area with increasing Ag content can be attributed to the progressive blocking of the HAP pores by the Ag metal.

Example 2

Overview of Catalytic Testing

The reaction was carried out at reaction temperatures between 175° C. and 350° C., more preferably between 200° C. and 275° C., and at atmospheric pressure using 200 mg catalyst. The method described in the present disclosure allows for the production of acetaldehyde selectively from ethanol at appropriate reaction temperatures.

The Reactor:

The reactor used for this process had three zones. The first zone was loaded with 3 mm diameter glass beads, acting as a pre-heater as well as a mixing zone for the ethanol and air feedstock. The second zone was loaded with the catalyst, which contacted with the vaporized feedstock from the first zone. The second zone was also the reaction zone in which the ethanol was converted to aldehyde in the presence of a catalyst. The third zone was the post-reaction zone. The reaction temperatures of the three zones were kept constant by three-heating zone heaters and the catalyst temperature was monitored using a thermocouple inside the catalytic bed.

Priming of the Catalyst:

Approximately 200 mg of catalyst (sieve size 400 µm to 250 µm) was diluted with equal amount of quartz and loaded into a down flow fixed bed stainless steel reactor. Prior to the reaction, the catalysts were in situ treated under $N_2$ gas at 175° C. for 1 hour.

Testing Procedure:

The disclosed experiments were carried out in a fixed bed reactor using 200 mg of catalyst (sieve size 400 µm to 250 µm). Ethanol (Fischer Scientific, HPLC grade) was fed into the reactor with a fixed flow rate of 0.025 mL/min at a weight hourly space velocity (WHSV) of 5.9 $h^{-1}$, with a simulated air mixture (60 mL/min) and preheated at 175° C. before entering into the reactor. All the gas flows were supplied into the system by employing pre-calibrated mass flow controllers. The reaction was carried out in the temperature range of 175° C. and 350° C., at atmospheric pressure. During the reaction, the ethanol flow rate was set at 0.025 mL/min with a corresponding weight hourly space velocity (WHSV) of 5.9 $h^{-1}$. Synthetic air with a flow rate of 60.0 mL/min was also introduced. The products were analysed by an online Gas Chromatography (GC) equipped with both a Flame Ionisation Detector (FID) and Thermal Conductivity Detector (TCD).

Data Analysis:

The analysis of the reaction products along with the reactants was performed using an online gas chromatograph (Agilent 6890) equipped with a flame ionization detector using a HP-5 capillary column- and thermal conductivity detector using a Hayesep D column. The GC was pre-calibrated using standards (reactant and products). The conversions of ethanol and selectivity to forming acetaldehyde were calculated as follows:

$$X_{EtOH}(\%) = \frac{N_{EtOH}^{in} - N_{EtOH}^{out}}{N_{EtOH}^{in}} *100 \quad (1)$$

$$S_{acetaldehyde}(\%) = \frac{N_{acetaldehyde}}{\sum_{i=1}^{n} N_{product_i}} *100 \quad (2)$$

$$Y_{acetaldehyde}(\%) = \frac{X_{EtOH} * S_{acetaldehyde}}{100} \quad (3)$$

where $X_{EtOH}$, is the conversion in mole percentage of ethanol, $N^{in}_{EtOH}$ is the number of moles of ethanol fed into the reactor and $N^{out}_{EtOH}$ is the number of moles of ethanol observed in the products. $S_{acetaldehyde}$, is the selectivity towards acetaldehyde product in mol %, $N_{acetaldehyde}$ is the number of moles of acetaldehyde product observed in the reaction products and $\Sigma_{i=1}^{n} N \, product_i$ is the total number of moles of reaction products. $Y_{acetaldehyde}$ is the yield of acetaldehyde in mold.

Example 3

Pure HAP and Ag-Doped HAP

Under similar reaction conditions as outlined in Example 2, HAP samples with various amounts of Ag-doping (0, 1, 3 and 6 at %) were tested for selective partial oxidation of ethanol at reaction temperatures between 200° C. and 350° C. This particular temperature range was selected, as the optimum temperature range for selective conversion of ethanol to aldehyde is between 200° C. and 300° C. 200 mg of catalyst, WHSV of 5.9 $h^{-1}$, ethanol flow rate of 0.025 mL/min and an oxygen flow rate of 12.0 mL/min was used. As seen in FIG. 1, of all the catalysts screened, the 3 at Ag-doped HAP and the 6 at % Ag-doped HAP exhibited the highest catalytic activity. It is also worth noting that the light off temperature, or the temperature at which total combustion and $CO_2$ production begins to occur, was observed to decrease with increasing Ag content of the HAP. It appears that high Ag content favours selective production of acetaldehyde at low reaction temperatures. Further, it can be seen that Ag-doped HAP catalysts invariably showed better acetaldehyde selectivity than pure HAP at temperatures up to 325° C.

Pure HAP (Control)

Figure 2:
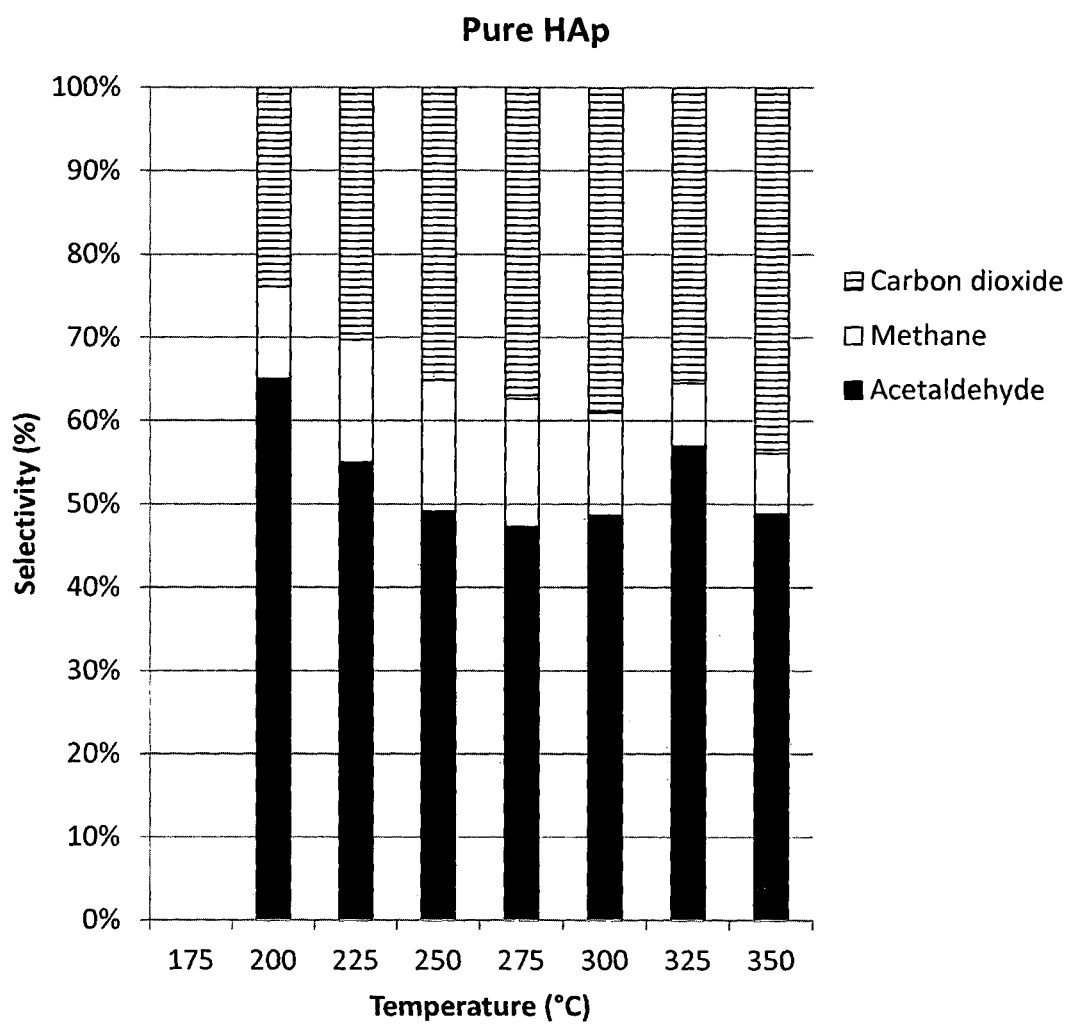
FIG. 2 is a bar chart showing the product selectivity of the ethanol conversion over pure stoichiometric HAP catalyst at reaction temperatures between 175° C. and 350° C.
Figure 3:
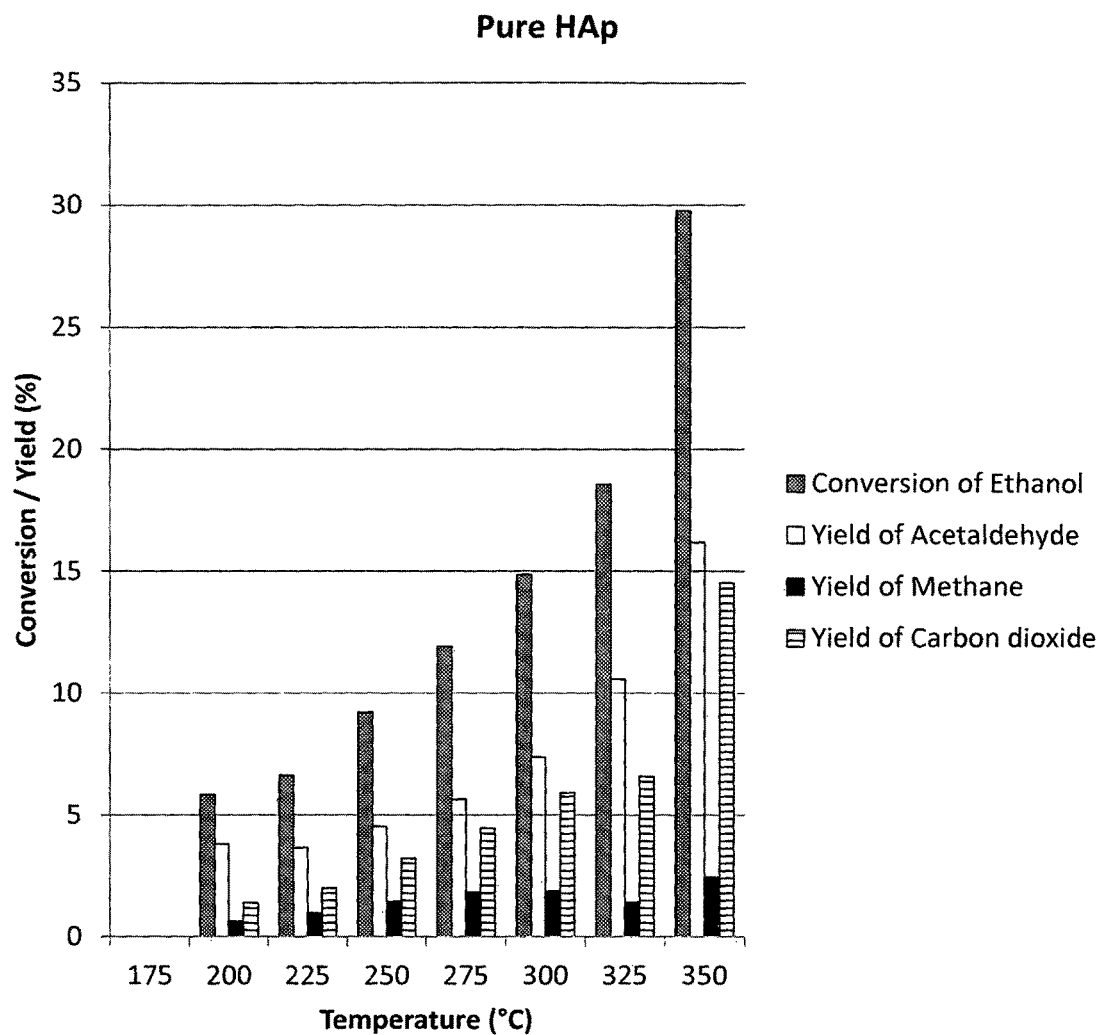
FIG. 3 is a bar graph showing ethanol conversion and acetaldehyde yield over pure stoichiometric HAP catalyst at reaction temperatures between 175° C. and 350° C.

Under similar reaction conditions as outlined in Example 2, the catalytic activity of pure HAP was tested, as shown in FIG. 2 and FIG. 3. In both FIG. 2 and FIG. 3, 200 mg of pure HAP catalyst, WHSV of 5.9 h$^{-1}$, ethanol flow rate of 0.025 mL/min and an oxygen flow rate of 12.0 mL/min was used. The pure HAP was shown to have maximum ethanol conversion of 28% at 350° C. Ethanol conversion was observed to increase with increasing temperature, but acetaldehyde selectivity decreased sharply in the temperature range of 200° C. to 275° C., and continued to decrease at higher temperatures. The pure HAP catalyst showed maximum acetaldehyde selectivity of approximately 65% at 200° C., but with a very low conversion of ethanol, at approximately 6%. Therefore, higher selectivity for acetaldehyde was observed at lower reaction temperatures. These results clearly indicate that pure HAP is not a suitable catalyst for selective conversion of ethanol to acetaldehyde.

1 at % Ag-Doped HAP

Figure 4:
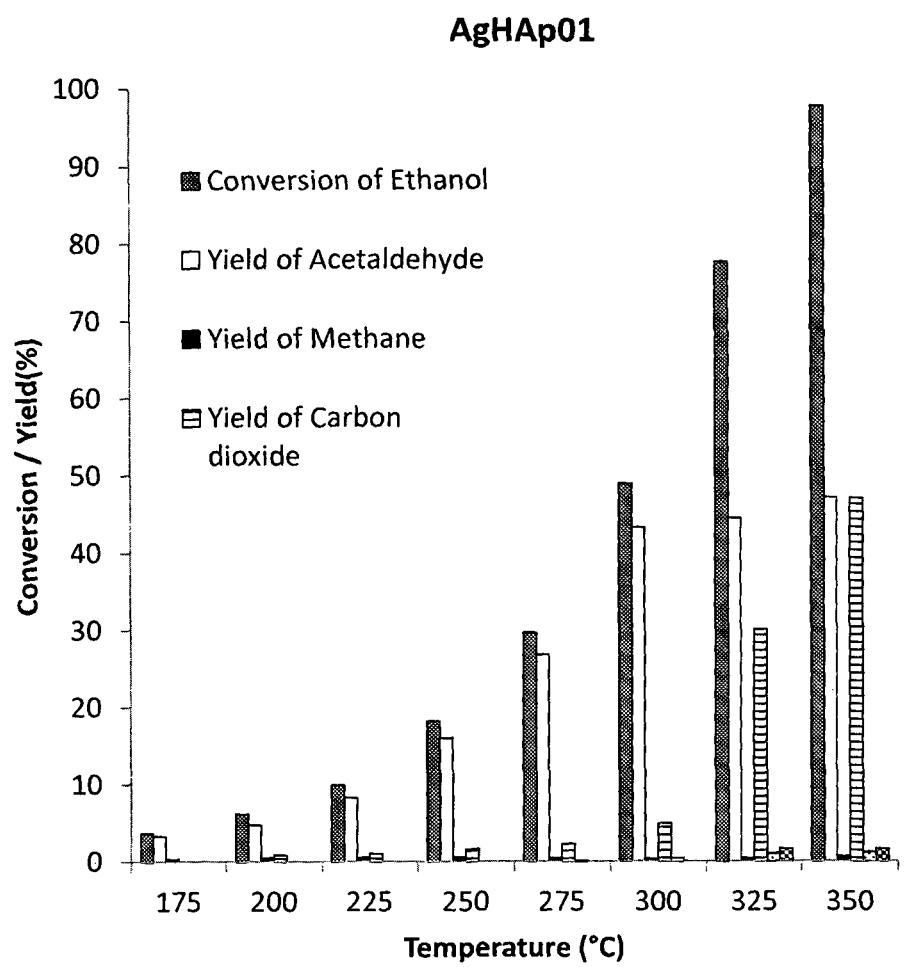
FIG. 4 is a bar graph showing ethanol conversion and acetaldehyde yield over 1 at % Ag-doped HAP at reaction temperatures between 175 and 350° C.
Figure 5:
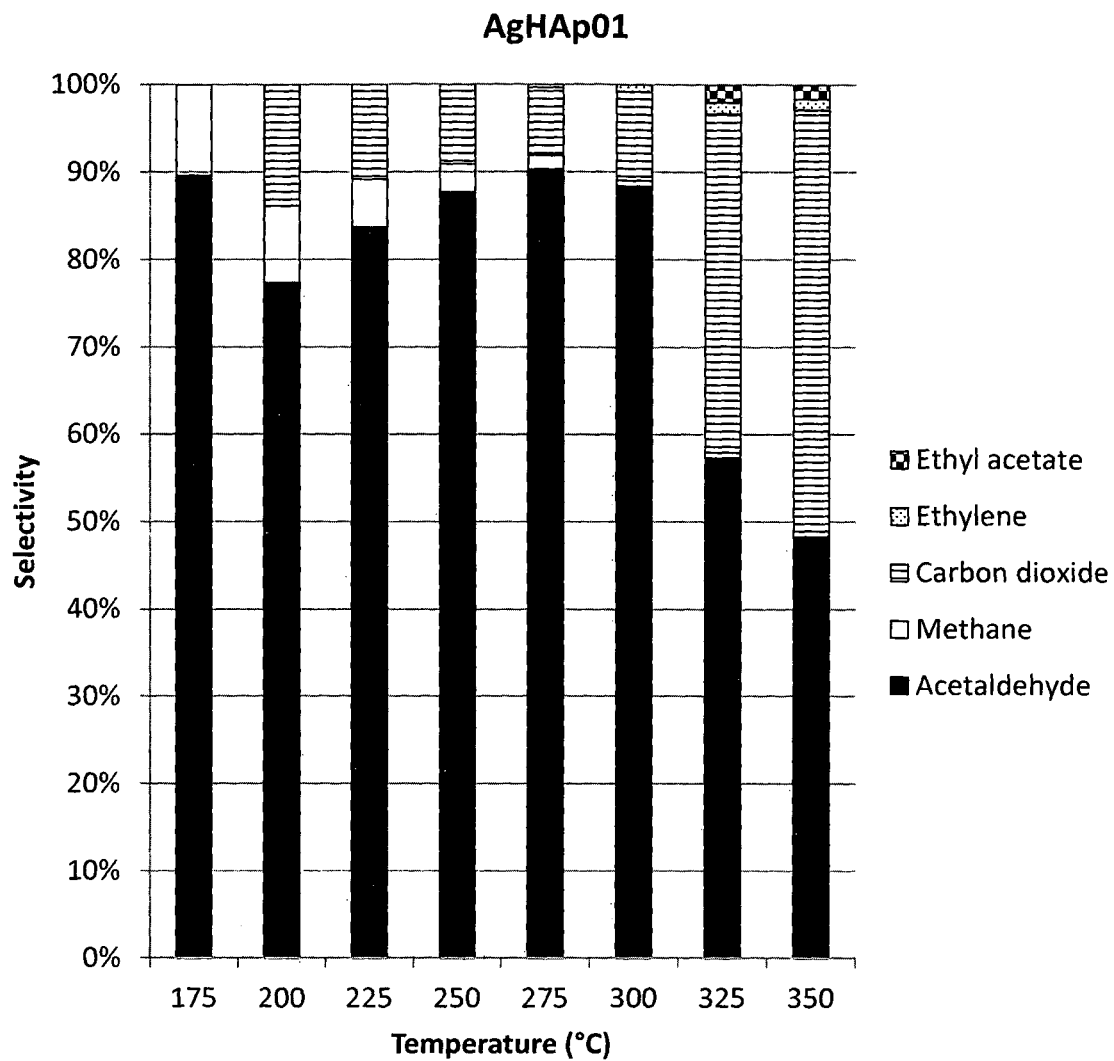
FIG. 5 is a bar chart showing product selectivity of the ethanol conversion over 1 at % Ag-doped HAP at reaction temperatures between 175° C. and 350° C.

Under similar reaction conditions as outlined in Example 2, the catalytic activity of 1 at Ag-doped HAP was tested, as shown in FIG. 4, and FIG. 5. In both FIG. 4 and FIG. 5, 200 mg of pure HAP catalyst, WHSV of 5.9 h$^{-1}$, ethanol flow rate of 0.025 mL/min and an oxygen flow rate of 12.0 mL/min was used. The 1 at % Ag-doped HAP was shown to have ethanol conversion of 49% at 300° C., which is significantly higher in comparison to pure HAP which was shown to have ethanol conversion of 15% at the same temperature. It is important to note that acetaldehyde selectivity did not reach 100% throughout the temperature range tested for both pure and 1 at % Ag-doped HAP. The maximum acetaldehyde selectivity observed for 1 at % Ag-doped HAP was 90% with an ethanol conversion of 30% at 275° C.

3 at % Ag-Doped HAP

Figure 6:
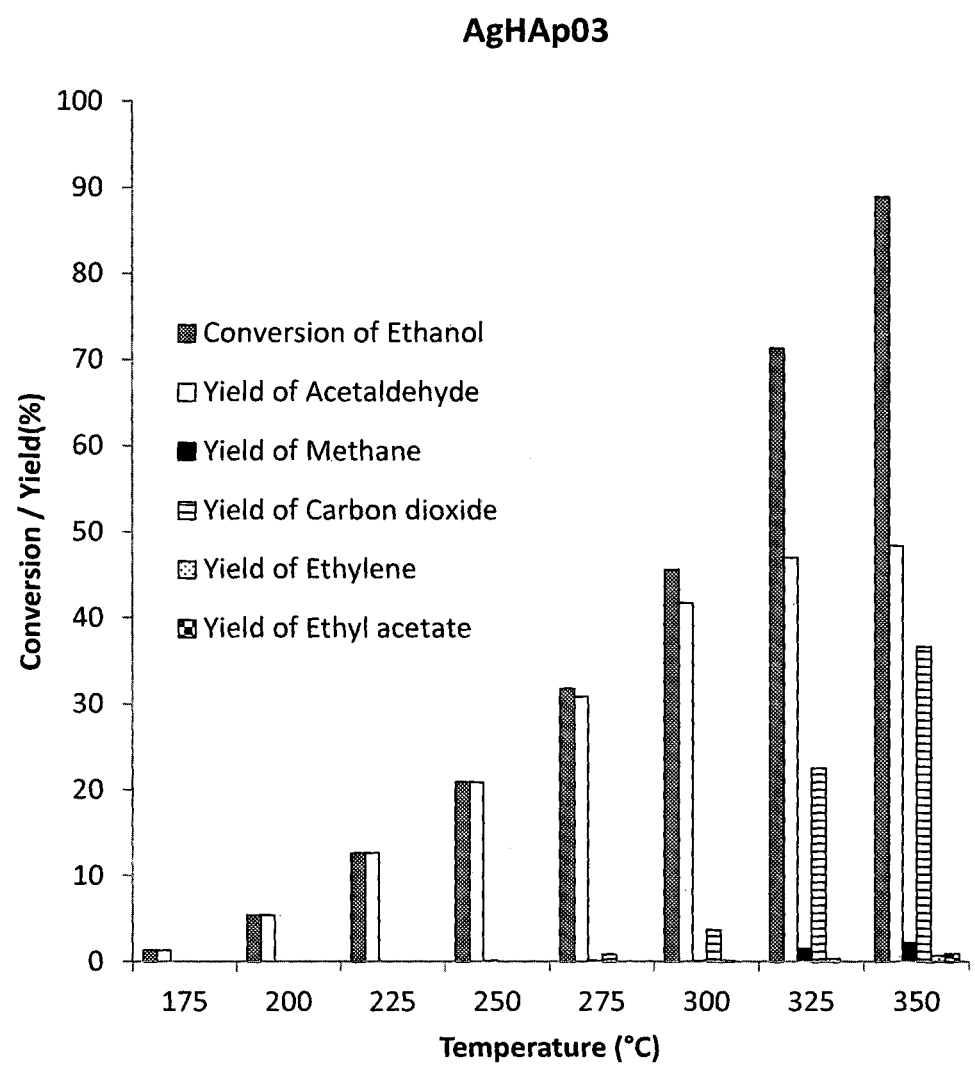
FIG. 6 is a bar graph showing ethanol conversion and acetaldehyde yield over 3 at % Ag-doped HAP at reaction temperatures between 175 and 350° C.
Figure 7:
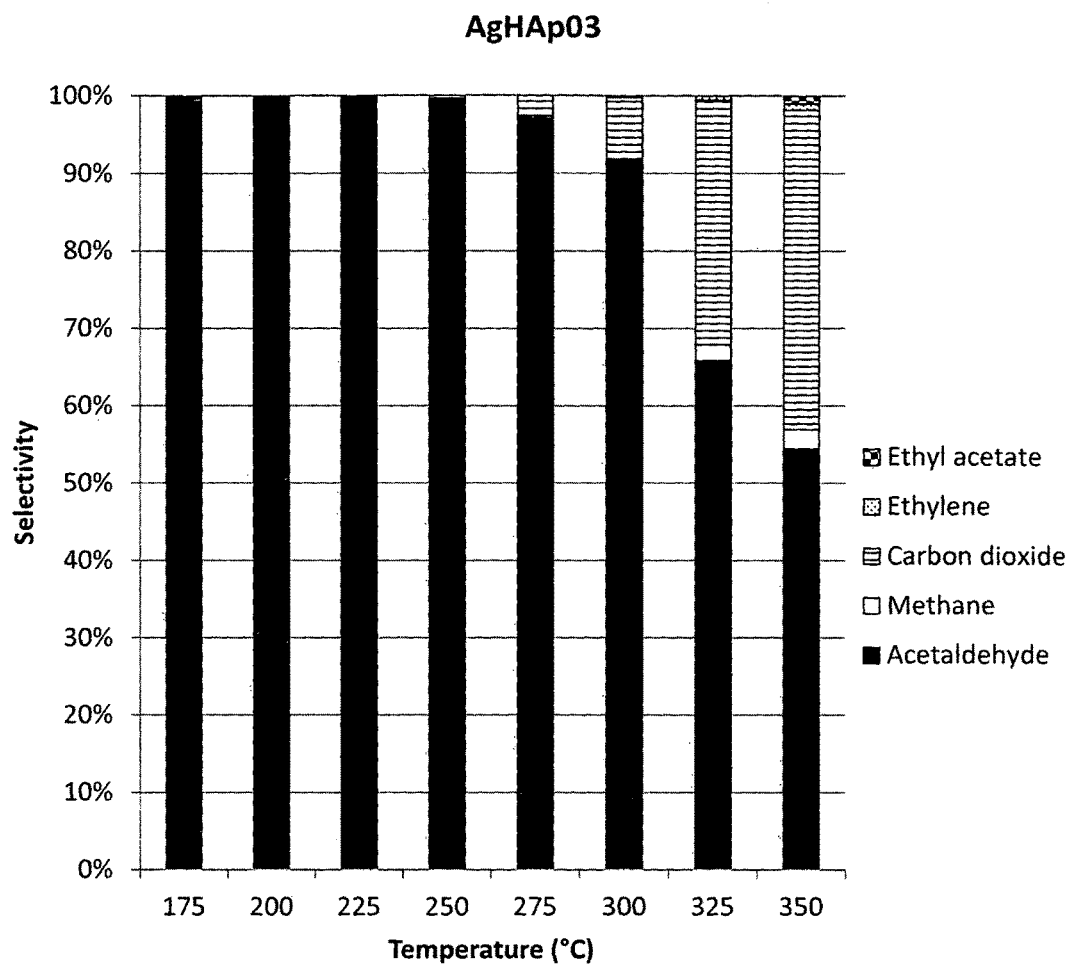
FIG. 7 is a bar chart showing product selectivity of the ethanol conversion over 3 at % Ag-doped HAP at reaction temperatures between 175° C. and 350° C.

Under similar reaction conditions as outlined in Example 2, the catalytic activity of 3 at % Ag-doped HAP was tested, as shown in FIG. 6 and FIG. 7. In both FIG. 6 and FIG. 7, 200 mg of pure HAP catalyst, WHSV of 5.9 h$^{-1}$, ethanol flow rate of 0.025 mL/min and an oxygen flow rate of 12.0 mL/min was used. The 3 at % Ag-doped HAP was shown to increase ethanol conversion as reaction temperature increased, but acetaldehyde selectivity decreased at temperatures greater than 250° C. Above this temperature, acetaldehyde yield decreased significantly. In contrast, $CO_2$ selectivity significantly increased at temperatures greater than 250° C. Ethanol conversion was observed to increase with increasing temperature, the maximum being at 87.4% at 350° C. However, acetaldehyde selectivity decreased with temperature due to considerable formation of $CO_2$ above 250° C. The maximum acetaldehyde yield was observed at 350° C.

6 at % Ag-Doped HAP

Figure 8:
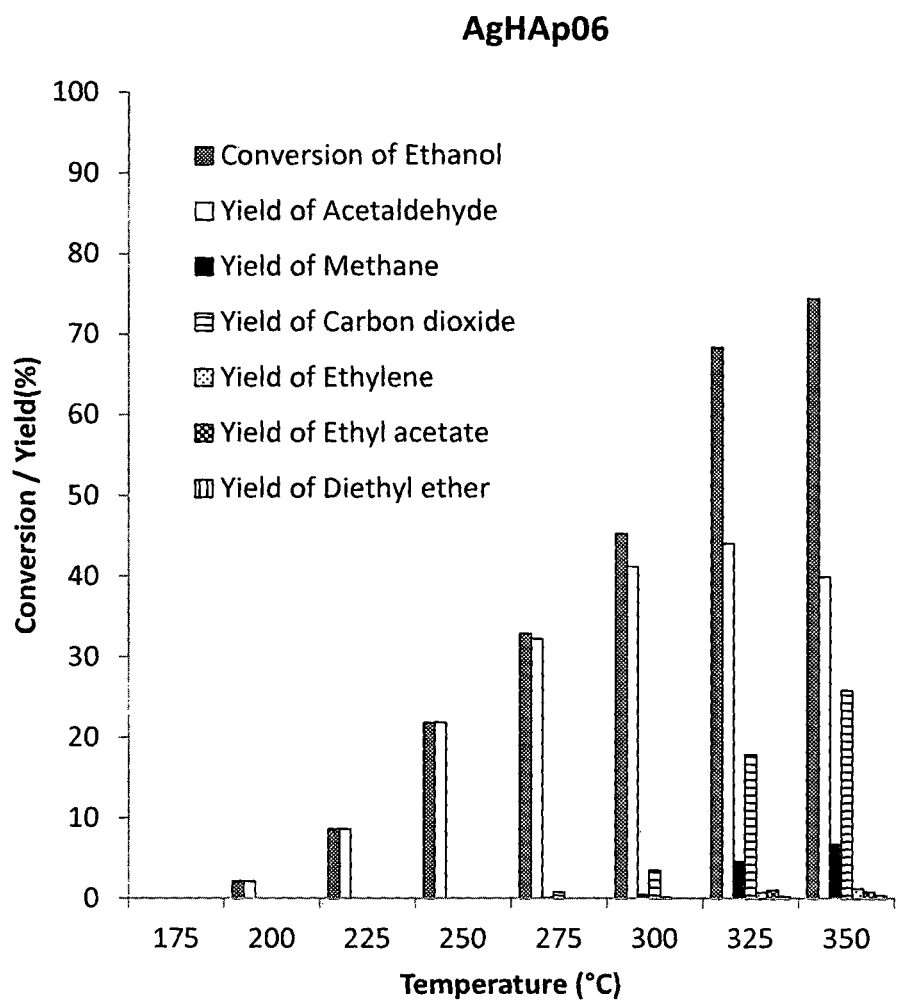
FIG. 8 is a bar chart showing product selectivity of the ethanol conversion over 6 at % Ag-doped HAP at reaction temperatures between 175° C. and 350° C.
Figure 9:
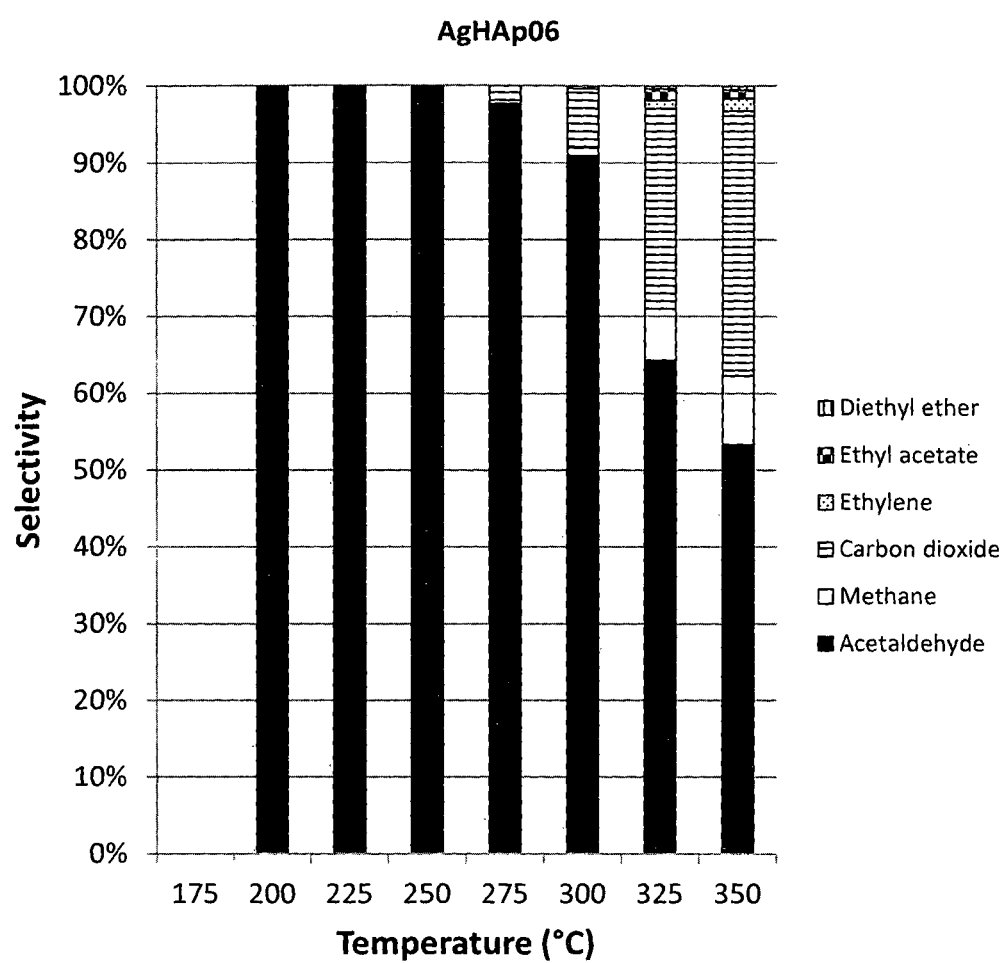
FIG. 9 is a bar chart showing ethanol conversion and acetaldehyde yield over 6 at Ag-doped HAP at reaction temperatures between 175° C. and 350° C.

Under similar reaction conditions as outlined in Example 2, the catalytic activity of 3 at % Ag-doped HAP was tested, as shown in FIG. 8 and FIG. 9. In both FIG. 8 and FIG. 9, 200 mg of pure HAP catalyst, WHSV of 5.9 h$^{-1}$, ethanol flow rate of 0.025 mL/min and an oxygen flow rate of 12.0 mL/min was used. The 6 at % Ag-doped HAP was shown to have similar catalytic activity to the 3 at Ag-doped HAP, with 100% acetaldehyde selectivity at a reaction temperature up to 250° C. However, there is less formation of $CO_2$ than with the 3 at Ag-doped HAP.

The Pure HAP catalyst exhibited ethanol conversion below 30% even at relatively high temperature (350 with a significant amount of acetaldehyde formation. In contrast, Ag-doped HAP catalysts exhibited high ethanol conversion and higher selectivity for acetaldehyde. In general, Ag-doped HAP showed better ethanol conversion and acetaldehyde selectivity compared to pure HAP, even at lower temperatures of reactions. It is clear that the selective conversion of ethanol to acetaldehyde can be improved by adding metals such as Ag to an HAP catalyst.

Example 4

Catalytic Stability of Ag-Doped HAP

Figure 10:
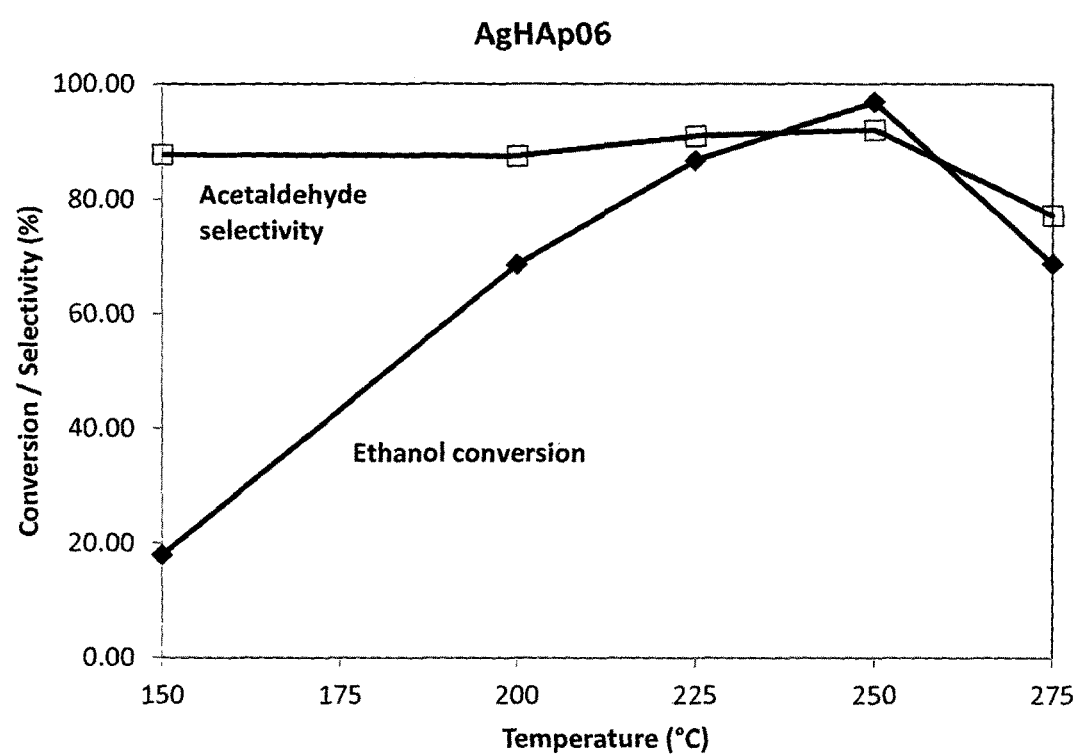
FIG. 10 is a graph showing the stability of the 6 at % Ag-doped HAP at 15 hours.

The 6 at % Ag-doped-HAP was tested for catalytic stability at reaction temperatures in the range of 150° C. to 350° C. Instead of using simulated air mixture, purified air was used for this experiment. An ethanol flow rate of 0.050 mL/min, WHSV of 11.8 h−1, and a purified air flow rate of 40 mL/min was used. The catalyst was observed to have stable activity over a 15 hours reaction time (data not shown). As shown in FIG. 10, at 225° C., acetaldehyde yield was 79% with an ethanol conversion of 87% and acetaldehyde selectivity of 91%. At a slightly higher temperature of 250° C., acetaldehyde yield was 89% with an ethanol conversion of 97% and acetaldehyde selectivity of 92%. At temperatures greater than 250° C., $CO_2$ began to form, decreasing the acetaldehyde yield.

Applications

The disclosed use of a metal-doped hydroxyapatite as a catalyst for converting an alcohol to an aldehyde may improve the conversion and selectivity of the reaction.

The disclosed use may be a useful alternative for converting ethanol to acetaldehyde.

The disclosed use may facilitate an oxidative dehydrogenation reaction of an alcohol to an aldehyde, improving the conversion, yield and selectivity of the reaction.

The disclosed use may allow the use of low-value feedstock such as ethanol to be converted to high-value chemicals such as acetaldehyde.

The disclosed use may contribute to more cost-effective production of high-value chemicals that use acetaldehyde as a precursor.

The disclosed use may allow the use of bio-ethanol as a feedstock, making the bulk production of acetaldehyde cost-effective and environmentally friendly.

The disclosed use may allow the use of inexpensive materials such as hydroxyapatite to be used as a catalyst, therefore making the bulk production of acetaldehyde more economical.

The disclosed use may be applied to developing a use for other metals and metal oxides supported on hydroxyapatite to catalyse other oxidation reactions.

The disclosed method may allow the reaction to be carried out at low temperatures below 300° C., decreasing the formation of by-products.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for converting an alcohol to an aldehyde, the method comprising:
   contacting an alcohol with a doped hydroxyapatite as a catalyst to form an aldehyde,
   wherein the doped hydroxyapatite has been doped with a dopant selected from the group consisting of a metal, a metal oxide, and mixtures thereof, wherein the metal is a transition metal selected from the group consisting of group 5 transition metals, group 11 transition metals, and chromium.

2. The method according to claim 1, wherein the transition metal comprises at least one of silver, gold, vanadium or chromium.

3. The method according to claim 1, wherein the metal oxide comprises an oxide of a transition metal, and optionally an oxide of a group 3, group 4, group 5, group 6, group 10, group 11 or group 12 transition metal.

4. The method according to claim 1, wherein the metal oxide comprises at least one of silver oxide, gold oxide, vanadium oxide, or chromium oxide.

5. The method according to claim 1, wherein the doped hydroxyapatite is doped with the dopant at an atomic percentage up to about 10 at % and optionally up to 6 at %.

6. The method according to claim 1, wherein the doped hydroxyapatite comprises a stoichiometric hydroxyapatite or a non-stoichiometric hydroxyapatite.

7. The method according to claim 1, wherein the doped hydroxyapatite comprises a non-stoichiometric hydroxyapatite having a Ca/P molar ratio of from about 1.45 to about 1.70 and optionally from about 1.50 to about 1.65.

8. The method according to claim 1, wherein the converting comprises oxidizing the alcohol to the aldehyde via an oxidative dehydrogenation reaction of the alcohol to the aldehyde.

9. The method according to claim 1, wherein the alcohol comprises a lower alcohol of 1 to 6 carbon atoms and optionally ethanol.

10. The method according to claim 1, wherein the aldehyde comprises a lower aldehyde of 1 to 6 carbon atoms and optionally acetaldehyde.

11. The method according to claim 1, wherein the contacting is performed at a temperature of from about 150° C. to about 350° C. and optionally from about 200° C. to about 275° C.

12. The method according to claim 1, wherein the contacting is performed at a pressure of from about 1 atm to about 20 atm and optionally at about 1 atm.

13. The method according to claim 1, wherein the contacting is performed at a weight hourly space velocity of from about 1 $h^{-1}$ to about 10 $h^{-1}$ and optionally from about 4 $h^{-1}$ to about 7 $h^{-1}$.

14. The method according to claim 1, wherein the doped hydroxyapatite is doped with the dopant at an atomic percentage of up to about 10 at %, and wherein the contacting is performed at a temperature of from about 150° C. to about 350° C.

15. The method according to claim 14, wherein the atomic percentage of the dopant is from about 1 at % to about 6 at % of the doped hydroxyapatite.

16. A method comprising:
   contacting an alcohol with a doped hydroxyapatite as a catalyst to form an aldehyde at a temperature of from about 150° C. to about 350° C.,
   wherein the doped hydroxyapatite has been doped with from about 0.1 at % to about 10 at % of a dopant selected from the group consisting of silver, gold, vanadium, chromium, silver oxide, gold oxide, vanadium oxide, chromium oxide, and mixtures thereof.

17. The method according to claim 16, wherein the doped hydroxyapatite is doped with about 1 at % to about 6 at % of the dopant.

18. The method according to claim 15, wherein the contacting is performed at a temperature below 300° C.

* * * * *

UNITED STATES PATENT AND TRADEMARK OFFICE
CERTIFICATE OF CORRECTION

Page 1 of 1

PATENT NO. : 9,586,884 B2
APPLICATION NO. : 14/780678
DATED : March 7, 2017
INVENTOR(S) : Ramesh et al.

It is certified that error appears in the above-identified patent and that said Letters Patent is hereby corrected as shown below:

In the Claims

In Column 15, Line 15, in Claim 2, delete "vanadium" and insert --vanadium,-- therefor In Column 16, Line 38, in Claim 18, delete "300° C." and insert --300 °C.-- therefor Signed and Sealed this
First Day of May, 2018

Andrei Iancu
*Director of the United States Patent and Trademark Office*